(12) United States Patent
Wright

(10) Patent No.: US 7,727,995 B2
(45) Date of Patent: Jun. 1, 2010

(54) ANTIHERPES DRUG COMBINATIONS

(75) Inventor: George E. Wright, Worcester, MA (US)

(73) Assignee: University of Massachusetts, Boston, MA (US)

( * ) Notice: Subject to any disclaimer, the term of this patent is extended or adjusted under 35 U.S.C. 154(b) by 973 days.

(21) Appl. No.: 10/767,019

(22) Filed: Jan. 29, 2004

(65) Prior Publication Data

US 2004/0259832 A1    Dec. 23, 2004

Related U.S. Application Data

(60) Provisional application No. 60/443,519, filed on Jan. 29, 2003.

(51) Int. Cl.
*A61K 31/522* (2006.01)
*C07D 473/30* (2006.01)

(52) U.S. Cl. .................. 514/263.37; 544/276

(58) Field of Classification Search .......... 514/261, 514/262
See application file for complete search history.

(56) References Cited

U.S. PATENT DOCUMENTS

| 5,137,724 A | 8/1992 | Balzarini et al. |
| 5,646,155 A | 7/1997 | Wright |
| 5,879,700 A * | 3/1999 | Hostetler ............... 424/443 |
| 6,015,573 A | 1/2000 | Hostetler |

OTHER PUBLICATIONS

Naesens et. al (Herpes, 8(1), 2001.*
Goodman & Gilman's: The Pharmacological Basis of Therapeutics, 10th Edition, McGraw-Hill Medical Publishing Division, 2001, pp. 54-56.*
Gilbert et al., "Resistance of herpesviruses to antiviral drugs: clinical impacts and molecular mechanisms" (2002) vol. 5 pp. 88-114.*
Nutter et al., "Demonstration of Viral Thymidine Kinase Inhibitor and it's Effect on Deoxynucleotide Metabloism in Cells Infected with Herpes Simplex Virus", Antimicrobial Agents and Chemotherapy, vol. 31, No. 3, pp. 368-374, Mar. 1987.
Klein et al., "Effect of a Thymidine Kinase Inhibitor (L-653,180) on Antiviral Treatment of Experimental Herpes Simplex Virus Infection in Mice", Anitviral Research, 14, pp. 207-214, 1990.
Manikowski et al., "Inhibition of Herpes Simplex Virus Thymidine Kinases by 2-Phenylamino-6-oxopurines and Related Compounds: Structure-Activity Relationships and Antiherpetic Activity in Vivo", J. Med. Chem., vol. 48, pp. 3919-3929, 2005.
Naesens et al., "Recent Developments in Herpesvirus Therapy", Herpes vol. 8, No. 1, 2001.
Xu et al., "Synethesis, Properties and Pharmacokinetic Studies of $N^2$-Phenylguanine Derivatives as Inhhibitors of Herpes Simplex Virus Thymidine Kinases", J. Med. Chem., vol. 38, pp. 49-57, 1995.
Klein et al., "Effect of a thymidine kinase inhibitor (L-653,180) on antiviral treatment of experimental herpes simplex virus infection in mice", Antiviral Research, vol. 14, pp. 207-214, 1990.
Reardon et al., "Herpes Simplex Virus Type I DNA Polymerase Mechanism of Inhibition by Acyclovir Triphosphate*", The Journal of Biological Chemistry, vol. 264, No. 13, pp. 7405-7411, May 1989.
Ashton et al., "A Potent. Selective, Non-Substrate Inhibitor Of HSV-1 Thymidine Kinase: (±)-9-[I (Z)-2-(Hydroxymethyl)Cyclohexyl]Methyl]Guanine And Related Compounds", Nucleosides, Nucleotides, vol. 8, pp. 1157-1158, 1989.
Nutter et al., "Demonstration of Viral Thymidine Kinase Inhibitor and Its Effect on Deoxynucleotide Metabolism in Cells Infected with Herpes Simplex Virus", Antimicrobial Agents and Chemotherapy, vol. 31, No. 3, Mar. 1987.

* cited by examiner

*Primary Examiner*—Shaojia Anna Jiang
*Assistant Examiner*—Eric S Olson
(74) *Attorney, Agent, or Firm*—Fish & Richardson P.C.

(57) ABSTRACT

Composition and methods are disclosed that include a synergistic combination of an inhibitor of Herpes simplex virus thymidine kinase, and an antiherpes substance.

22 Claims, No Drawings

ANTIHERPES DRUG COMBINATIONS

CROSS REFERENCE TO RELATED APPLICATIONS

This application claims the benefit of priority from U.S. Provisional Patent Application No. 60/443,519, filed on Jan. 29, 2003, the contents of which is incorporated herein by reference in its entirety.

STATEMENT AS TO FEDERALLY SPONSORED RESEARCH

The invention described herein was supported in part by SBIR grant number AI43170-01-03 from the National Institutes of Health. The government thus has certain rights in the invention.

TECHNICAL FIELD

This invention relates to antiherpes compositions, more particularly to synergistic combinations of inhibitors of Herpes simplex virus-specific thymidine kinase, and antiherpes drugs. Such combinations are useful in treating recurrent Herpes simplex infections and encephalitis.

BACKGROUND

Herpes simplex viruses types 1 and 2 (HSV1 and HSV2) infect skin and mucous membranes to cause acute lesions, which resolve within a matter of days. However, during the course of this infection virus is transported to the neurons that innervate the locally infected site and establish a lifelong latent persistence. Generally, the acute infections of the mouth, eye, and other facial regions are caused by HSV1, with the establishment of latency in the trigeminal ganglia, whereas acute infections of the genital areas are due to HSV2, with the establishment of latency in the lumbar and sacral ganglia. In both cases, lifelong latency is punctuated periodically by production of infectious virions in the ganglia, transport to the innervated epithelial tissue, and bouts of acute virus replication, shedding of infectious virus from the acutely infected site, and perhaps local lesion formation. These lesions are the familiar cold sores, which occur around the lips, herpes keratitis of the eye, and the venereal disease of the anal/genital region.

In addition to these common clinical experiences, herpes simplex viruses may also cause life-threatening encephalitis both in neonates, usually the result of massive virus exposure during birth, and in immuno-compromised adults. Herpetic encephalitis results in high mortality, and survivors are often severely handicapped. Herpetic encephalitis occurs in about 3000 newborns each year in the USA. Often this results because of massive exposure of the neonate to virus (usually HSV2) shed in the birth canal of the infected mother, and is of greatest probability if the membranes have ruptured and if the mother is experiencing a primary genital herpetic infection. The infected newborn may experience localized skin and ocular lesions, viremia, and localized central nervous system lesion development, usually starting within 6 days of birth. If infection results in disseminated disease, central nervous system (CNS) disease occurs in up to 50% of the infants and can result in 75% mortality. For the survivors of CNS involvement the outcome is bleak, with psychomotor retardation in 50 to 75% of the survivors.

The compound 2-phenylamino-6-oxo-9-(4-hydroxybutyl) purine, HBPG (U.S. Pat. No. 5,646,155) has been shown to reduce the frequency of hyperthermia-induced HSV1 and HSV2 reactivation in mice and reduce the amount of viral DNA in the relevant nerve ganglia. In addition, HBPG has been shown to reduce the frequency of recurrent ocular HSV1 disease in squirrel monkeys.

SUMMARY OF THE INVENTION

The invention is based, in part, on the discovery that combinations of certain antiherpes drugs have unexpected synergistic activity against recurrent Herpes simplex infections and Herpes simplex encephalitis. Such combinations include an inhibitor of Herpes simplex virus-specific thymidine kinase and an antiherpetic compound. The antiherpetic compounds inhibit viral DNA replication, e.g., by inhibiting viral DNA polymerase. The combinations can be administered parenterally, orally, or topically to inhibit or to treat herpetic recurrences, or parenterally to treat herpes encephalitis and neonatal herpes diseases in animals or humans.

In general, the invention features pharmaceutical compositions including a combination as described above, methods for inhibiting herpesvirus reactivation, and methods for therapeutically or prophylactically treating an animal with a latent herpesvirus infection or encephalitis. The inhibitor compounds described herein inhibit Herpes simplex type 1, Herpes simplex type 2, and *Varicella zoster* virus-encoded thymidine kinases (TK). The compounds inhibit the growth of the viruses in nerve cells, including those of the central nervous system and sensory nerve ganglia. The invention further features pharmaceutical compositions containing these compounds; methods for inhibiting the growth of herpesviruses using these compounds; and methods for treating animals with, or susceptible to, herpesvirus infections.

In one aspect, the invention features a composition including a combination of a) an inhibitor of Herpes simplex virus thymidine kinase, and b) an antiherpes substance that inhibits viral DNA replication, e.g., by inhibiting viral DNA polymerase and includes one or more of (1) a pre-phosphorylated or phosphonate nucleoside analog; (2) a pyrophosphate analog; and (3) a nucleoside analog, or any combination thereof, or an ester, salt or solvate thereof, optionally, in a pharmaceutically acceptable carrier. For example, the pre-phosphorylated or phosphonate nucleoside analog can be acyclovir monophosphate, ganciclovir monophosphate, cidofovir, or PMEA (9-(phosphonomethoxyethyl)adenine), or an ester, salt or solvate thereof. The pyrophosphate analog can be phosphonoacetate, phosphonoformate (i.e., foscamet), or an ester, salt or solvate thereof. The nucleoside analog can be acyclovir, famiciclovir, or ganciclovir, or an ester, salt or solvate thereof.

The composition can include a pharmaceutically acceptable carrier such as sterile water, saline, polyalkylene glycols, vegetable oils, hydrogenated naphthalenes, biocompatible polymers, biodegradable polymers, or mixtures thereof. The biodegradable polymer can be, for example, polycaprolactone, polydecalactone, poly(sebacic anhydride), sebacic acid-co-1,3-bis(carboxyphenoxypropane), sebacic acid-co-1,6-bis(carboxyphenoxyhexane), dedecanoic-co-1,3-bis (carboxyphenoxypropane), dedecanoic-co-1,6-bis(carboxyphenoxyhexane), albumin and derivatives, gelatin and derivatives, starch and derivatives, gum arabic, cellulose and derivatives, polysorbate and derivatives, agarose, lectins, galactose, polyurethanes, polyvinylalcohol, functionalized polymers and copolymers of lactic and glycolic acid, lactic acid homopolymer, glycolic acid copolymer, copolymers of lactic acid and glycolic acid, polyhydroxybutyrate, polyhydroxyalkanoic acid, or mixtures thereof. The biodegradable polymer can be in the form of a particle, and the particle can include multiple walls.

In these compositions, the antiherpes substance can be one that does not require phosphorylation by Herpes simplex virus thymidine kinase to be active. In certain embodiments, the inhibitor of Herpes simplex virus thymidine kinase can be selected from the group consisting of 2-phenylamino-9-substituted-6-oxopurines and 2-phenylamino-9H-6-oxopurines, or an ester, salt or solvate thereof. The thymidine kinase inhibitor can be 2-phenylamino-9-(4-hydroxybutyl)-6-oxopurine (i.e., HBPG), or an ester, salt or solvate thereof.

In other aspects, the invention features dosage forms for parenteral or oral use, or creams, lotions, gels, ointments, plasters, sticks, or pens that contain the new pharmaceutical compositions.

In another aspect, the invention includes methods for the prophylaxis and/or treatment of recurrent Herpes simplex virus infections of the skin or mucous membranes, or Herpes simplex virus encephalitis, in a mammal, by administering to the mammal, in combination, a therapeutic dose, e.g., a synergistic dose, of a) an inhibitor of Herpes simplex virus thymidine kinase, and b) an antiherpes substance, for example, including one or more of (1) a pre-phosphorylated or phosphonate nucleoside analog; (2) a pyrophosphate analog; and (3) a nucleoside analog, or any combination thereof, or an ester, salt or solvate thereof. For example, the thymidine kinase inhibitor can be selected from the group consisting of 2-phenylamino-9-(4-hydroxybutyl)-6-oxopurine, 2-(3-trifluoromethylphenylamino)-6-oxopurine, or an ester, salt or solvate thereof. The Herpes simplex virus can be type 1 or 2, or the herpesvirus can be *Varicella zoster* virus. The infection treated can be in the skin, in a mucous membrane, or can be in the neurological system. The dose can be administered topically to an area of the body, such as the eyes, mouth or genital areas.

In other embodiments, the invention includes methods for inhibiting growth of Herpes simplex virus in a mammal, by administering to the mammal, in combination, a therapeutic dose of a) an inhibitor of Herpes simplex virus thymidine kinase, and b) an antiherpes substance.

In another aspect, the invention features a kit for treatment of a Herpes simplex virus infection in a mammal. The kit includes a) an inhibitor of Herpes simplex virus thymidine kinase, b) an antiherpes substance, and c) instructions for administering the two compositions concurrently or within a sufficiently close time to achieve coexistent concentrations of (a) and (b) in subject.

The new methods and compositions are useful for treating recurrent herpesvirus infections and encephalitis. The methods for treating (e.g., inhibiting the growth) of herpes viruses involve administering to the subject, e.g., a human or other mammal (dogs, cats, horses, sheep, goats, pigs, cows) or other animal, one or more of the new compositions in an amount sufficient to inhibit growth of the virus. By "inhibiting the growth" is meant reducing the virus growth rate by at least 80%. In certain embodiments, the growth can be inhibited by 90%, 95%, or even 99% or more. The degree of inhibition can be ascertained by an in vitro co-cultivation assay, e.g., by incubating latently infected nerve ganglia with host cells by a standard liquid culture technique. Compounds showing inhibition of virus reactivation in this assay at suitable concentrations, e.g., <1 µM, are useful as therapeutic agents. In the context of inhibiting herpesvirus growth, "effective amount" of a compound means an amount which, when administered in vivo or in vitro, will achieve a level of inhibition of at least 80%.

The method for treating an animal or mammal with a herpesvirus infection involves administering a therapeutically effective amount of a composition of the invention. By "therapeutically effective amount" is meant an amount which, when administered to an animal or human subject in need, will alleviate at least some of the symptoms of a herpesvirus infection. In the context of prophylaxis, a "therapeutically effective amount" is an amount which, when administered to an animal or human subject susceptible to herpesvirus recurrences, will inhibit or reduce the likelihood of such recurrent infections. By "synergistic" is meant more than an additive effect.

By "a subject susceptible to a recurrent herpesvirus infection" is meant an animal or human that is at increased risk, relative to the general population, of having recurrent herpes infections. Examples of such animals and humans include those who have frequent herpes recurrences, those who have recently undergone a surgical procedure, or immuno-compromised humans, e.g., those with AIDS (acquired immunodeficiency syndrome). Such animals and humans can be identified using methods known to one of ordinary skill in the art.

By "substituted" is meant that one or more hydrogen atoms of a compound or portion of a compound are replaced by substituents, including, but not limited to, $C_{1-4}$ alkyl, $C_{1-6}$ cycloalkyl, hydroxyl, $C_{1-4}$ alkoxyl, amino, carboxyl, halo, cyano, azido, $C_{6-12}$ aryl, $C_{7-20}$ arylalkyl, $C_{4-6}$ heteroaryl, (CO)—$C_{1-6}$ alkyl, (CO)—$C_{1-6}$ aryl, $(SO_2)$—$C_{1-6}$ alkyl, $(SO_3)$—$C_{1-6}$ alkyl, $(SO_2)$—$C_{6-12}$ aryl, $(SO_3)$—$C_{6-12}$ aryl, $(SO_2)$—$C_{4-12}$ heteroaryl, $(SO_3)$—$C_{4-12}$ heteroaryl. The substituents can in turn be substituted with functional groups, including, but not limited to, halo, trifluoromethyl, hydroxyl, and carboxyl.

By "pharmaceutically acceptable salts" are meant those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids such as oxalic, while not themselves pharmaceutically acceptable, may be useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and $NR_4^+$ (where R is $C_{1-4}$ alkyl) salts. Useful salts include hydrochlorides, hydrobromides, sulfates, mesylates, maleates, and fumarates. References hereinafter to the new compounds includes compounds of the general formulae shown, as well as their pharmaceutically acceptable salts.

The new combinations of compounds described herein may contain functional groups that increase the water solubility of the compounds, facilitating their bioavailability, absorption, and distribution in humans and animals, without interfering with their inhibition of growth and reactivation of Herpes virus. Alternatively, the compounds form salts that are relatively water-soluble.

In addition, the low toxicity of these compounds to humans, mammals, and other animals endows this class of agents with the characteristics required of therapeutic antiherpes drugs. The compounds target an essential enzyme in Herpes virus reactivation and replication in nerve cells that has not previously been a target for any marketed antiviral drug.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying description below. Other features, objects, and advantages of the invention will be apparent from the description and from the claims.

DETAILED DESCRIPTION

This invention, in several aspects, provides pharmaceutical compositions including, and methods for using, the compounds described herein. Such methods include treating subjects with a latent herpesvirus infection by administering to the subject, e.g., animal or human, a therapeutically effective amount of a compound or composition as described herein, and a method of treating a subject with a herpesvirus infection of the brain, the method comprising administering to the subject a therapeutically effective amount of a the new compounds. Other methods for using the news compounds and compositions are available and are expressly included as a part of this invention.

Mechanism of Action

Herpes simplex viruses (HSV) establish lifelong latent infections in humans following an initial infection. Reactivation of the virus from the seat of latency—sensory nerve ganglia—results in recurrent disease in susceptible individuals. Except for active antiviral therapy which inhibits viral DNA replication, e.g., by inhibiting viral DNA polymerase and prophylactic acyclovir in certain cases, there are no drugs available to prevent recurrences or to prevent asymptomatic viral shedding and infectivity. In addition, although they are relatively rare diseases, HSV encephalitis and related neonatal herpes infections are still associated with high morbidity and with permanent neurological sequelae, despite the availability of antiviral drugs acting on peripheral tissues.

Among possible viral functions involved in HSV latency and neurovirulence, evidence suggests that viral thymidine kinase (TK) expression is required for both reactivation of latent HSV and for encephalitis. HSV TKs do not appear to be essential for viral replication in peripheral host cells (Tenser, "Role of herpes simplex virus thymidine kinase expression in viral pathogenesis and latency," *Intervirology*, 32:76-92, 1991). Reactivation of HSV from latent infections, however, appears to require several virus specific enzymes, notably TK, uracil-DNA glycosylase, and ribonucleotide reductase. Virus strains that lack functional TK do not reactivate, although such TK⁻ viruses do establish latency. These observations lead us to believe that HSV TK is required for reactivation of virus from the latent state. In addition, TK⁻ HSV strains produce less virulent disease than parental viruses, especially in nondividing tissues, such as in the brain.

TK Inhibitors as Anti-HSV Reactivation Compounds

The first evidence that a viral TK inhibitor might prevent HSV reactivation was established using two $N^2$-phenylguanines in an explant-cocultivation experiment. Trigeminal ganglia were removed from mice in which HSV1 latency had been established following ocular infections and incubated on Vero cell cultures. The inhibitors, $N^2$-(m-trifluoromethylphenyl)guanine (m-CF₃PG) and $N^2$-phenyl-2'-deoxyguanosine (PhdG), at 150 μM significantly reduced the number of ganglia producing virus compared to control ganglia (see, Leib et al., "Specific inhibitors of herpes simplex thymidine kinase diminish reactivation of latent virus from explanted murine ganglia," *Antimicr. Agents Chemothe.*, 34:1285-1286, 1990). A lead compound (U.S. Pat. No. 5,646,155)—$N^2$-phenyl-9-(4-hydroxybutyl)guanine (HBPG)—showed clear efficacy in preventing recurrence of ocular HSV1 disease in the mouse (Gebhardt et al., *Antiviral Res.*, 30:87-94, 1996) and squirrel monkey models of latent HSV1 infections (Kaufman et al., *Antiviral Res.*, 33:65-72, 1996).

New TK inhibitors can also be used in the combinations and methods disclosed herein.

Drug Combinations

There are a number of possible combinations of drugs or compounds that can be used according to the new methods. In addition to a herpes simplex virus TK inhibitor discussed above, each combination also includes an antiherpes substance, e.g., a substance that inhibits viral DNA replication, e.g., by inhibiting viral DNA polymerase. These substances may be known and fall into at least three categories: (1) pre-phosphorylated or a phosphonate nucleoside analog such as acyclovir monophosphate, ganciclovir monophosphate, cidofovir, and 9-(phosphonomethoxyethyl)adenine (PMEA); (2) pyrophosphate analogs such as phosphonoacetate and phosphonoformate (foscarnet); and (3) nucleoside analogs such as acyclovir and ganciclovir. In each category, the drug can also be an ester, salt, or solvate of the known drugs. New antiherpes substances can also be used in the combinations and methods disclosed herein.

Therapeutic Administration of Compositions

The compound combinations can be formulated for pharmaceutical, veterinary, and tissue culture use, optionally together with an acceptable diluent, carrier, or excipient, and/or in unit dosage form. In using the combination compositions of the invention, conventional pharmaceutical, veterinary, or culture practices can be employed to provide suitable formulations or compositions, all of which are encompassed by the pharmaceutical compositions of this invention. The compounds of the combination can be delivered in series, or simultaneously (or approximately at the same time) in one composition, or as two separate compounds. If delivered in series, they should delivered be sufficiently close together in time to achieve coexistent concentration in the subject. For example, the compounds can be delivered from 0 to 4 hours apart, e.g., 1, 2, 5, 10, 15, 20, 30 or more minutes apart, or 1, 2, or 3 hours apart. The goal is to achieve a high concentration, e.g., the maximum concentration, in the infected tissue of both drugs in the combination at the same time, based on dosage, route of delivery, and half-life of particular drugs.

For human or animal use, the new formulations can be administered by parenteral administration, for example, intravenous, subcutaneous, intramuscular, intraorbital, ophthalmic, intraventricular, intracranial, intracapsular, intraspinal, intracisternal, or intraperitoneal administration, or by intranasal, aerosol, scarification, oral, buccal, rectal, vaginal, or topical administration. The formulations described herein can also be administered as surgical implants, which release the compounds, either as a bolus or slowly over a pre-selected period of time.

Without limitation, parenteral formulations can be, for example, in the form of liquid solutions or suspensions; for oral administration, formulations can be, for example, in the form of tablets, capsules, liquid solutions and suspensions (wherein such solutions and suspensions are particularly for formulations intended for pediatric use); and for intranasal administration, the formulations can be, for example, in the form of powders, nasal drops, or aerosols. Other suitable formulations for parenteral, oral, or intranasal delivery of the compounds of this invention will be well known to those of ordinary skill in the art.

Methods well known in the art for making formulations can be found in, for example, "Remington's Pharmaceutical Sciences." Formulations for parenteral administration may contain as excipients sterile water or saline, polyalkylene glycols (available from DOW and BASF), such as polyethylene glycol, oils of vegetable origin, hydrogenated naphthalenes, biocompatible polymers, and biodegradable polymers, e.g., lactide polymers. Polyoxyethylene-polyoxypropylene copolymers can be used to control the release of the present compounds. Other potentially useful parenteral delivery systems for the new compositions include ethylene-vinyl acetate copolymer particles, osmotic pumps, implantable infusion systems, liposomes, and biodegradable microspheres, including multi-wall microspheres, such as those described in U.S. Pat. Nos. 4,861,627, 5,718,921 and 5,912,017. Formulations for inhalation may contain lactose as an excipient, or can be aqueous solutions containing, for example, polyoxyethylene-9-lauryl ether, glycocholate and deoxycholate, or can be oily solutions for administration in the form of nasal drops, or can be gels to be applied intranasally. Formulations for parenteral administration may also include glycocholate for buccal administration, methoxysalicylate for rectal administration, or citric acid for vaginal administration. Formulations for topical administration are in the form of creams, pastes, gels, or lotions.

The concentration of the compounds in the new formulations will vary depending upon a number of factors, including the dosage to be administered, and the route of administration. In general, the compounds of the invention can be provided in an aqueous physiological buffer solution containing about 0.1 to 10% w/v compound for parenteral administration. General dose ranges are from about 0.01 mg/kg to about 1 g/kg of body weight per day, e.g., from about 0.05 or 0.1 mg/kg to 100 mg/kg of body weight per day. The dosage to be administered depends upon the type and extent of progression of the infection being addressed, the overall health of the patient, and the route of administration. For topical and oral administration, formulations and dosages can be similar to those used for other antibiotic drugs, e.g., erythromycin.

In one embodiment, a combination of the invention is administered to an animal (e.g., swine, chicken, cow, horse, or other commercially relevant livestock) or to a human patient who has been diagnosed with a Herpes simplex infection. The combinations can also be administered to the animal or human to reduce the likelihood of recurrence of a Herpes simplex virus infection, particularly in an animal or human susceptible to such infections (including, without limitation, a human patient who is immuno-deficient or immuno-compromised or one who has recently undergone a medical procedure). In other embodiments, combinations can be administered to animals or humans diagnosed with Herpes simplex encephalitis or neonatal herpes.

The compounds can be administered both prophylactically and after infection has occurred. Prophylaxis can be most appropriate for immuno-compromised animals and human patients, and for animals and patients following surgery or dental procedures. This list of relevant conditions for application of the methods of the invention is not intended to be limiting, and any appropriate infection responsive to the compounds can be treated using the methods and/or compounds described herein. The new compositions can be administered topically before infection to reduce the risk of infection, or after infection to reduce the severity and longevity of the infection. Topical application is suitable for such conditions as keratitis, sores around the mouth, and vaginitis. Parenteral treatment is suitable for the treatment of herpes encephalitis and neonatal herpes.

EXAMPLES

The following specific examples are to be construed as merely illustrative, and not limitative of the remainder of the disclosure in any way.

Example 1

Inhibition of HSV Reactivation Model in Mice

Mice in which latent HSV1 infections have been established by ocular infection are treated with a test drug combination in sterile water by intravenous injection. At a specified time following drug treatment, the animals are placed in water at 42° C. for ten minutes to reactivate the virus through hyperthermia, and are then returned to their cages for 24 hours. Control animals are treated similarly, but have no drug is administered. After the 24 hour period, treated and control mice are sacrificed, their corneas swabbed and then minced, and the trigeminal ganglia are excised. The swabs and minced eyes are plated on CV-1 cells, and virus production measured. The results are analyzed to determine if reduction in infectious virus recovery that is dose-dependent has occurred.

Quantitative PCR (polymerase chain reaction) is used to measure virus-specific DNA in trigeminal ganglia of the mice in the experiment described above. The data are analyzed to determine if the drug had reduced viral DNA expressed in ganglia in treated animals relative to controls.

Example 2

Inhibition of HSV Reactivation Model in Squirrel Monkeys

The corneas of squirrel monkeys are infected with HSV-1 (strain Rodanus) as described by Varnell et al., Invest. Ophthalmol. Vis. Sci., 36:1181-1183 (1995). All corneas show typical herpetic dendritic lesions 3 or 4 days after infection; 15 days after infection, all corneas are typically clear. The monkeys are divided into two groups. The experimental group received a test drug combination and the control group receives vehicle alone, both by the intraperitoneal route. Treatment is administered over 25 days to both groups. The animals are neither tranquilized nor anesthetized for the treatments, but only hand restrained. All corneas are stained with sodium fluorescein and examined daily each weekday over the 25-day treatment period (total examination days=18) and for 25 days after cessation of treatment (total additional examination days=18) by an observer masked as to the treatment group. Observed lesions are typically true recurrences in that the earlier lesions will have completely healed and the new lesions develop in slightly different areas. Results of these experiments are reported as the ratio of the number of eyes with recurrent disease to the total number of eyes, and statistical significance is determined by one-tailed chi-squared analysis. In addition, cumulative total recurrences in both the treatment and control groups is compared, both during and following cessation of treatment.

Example 3

Inhibition of HSV Encephalitis in Mice

BALB/c female mice at 6 weeks of age were anesthetized, their corneas lightly scratched with a 27-gauge needle, and 3 µl of infectious virus (McKrae strain of HSV-1 or G strain of HSV-2; 5×10$^5$ PFU) was placed on each cornea. At the time of infection, groups of ten animals were given 0.1 ml injections i.p. of vehicle (corn oil) or test drug or drug combination (e.g., HBPG or foscarnet or both) in vehicle at indicated concentrations, and the animals were returned to their cages and allowed to recover from anesthesia. Treatment was repeated by a regimen optimal for the drug combination and dose. Animals were observed daily for 30 days, and the day of death of each animal was recorded. The results are summarized in Tables 1 and 2 below.

Table 1 illustrates the dose-response relationships for treatment of HSV1 and HSV2 encephalitis when the individual drugs were given by intraperitoneal (ip) injection.

TABLE 1

Comparison of effect of HBPG and foscarnet on HSV encephalitis in mice

| Treatment | Dose, mg/kg, ip Twice daily, 5 days | Survivors/treated (%) HSV1 | HSV2 |
|---|---|---|---|
| Corn oil (vehicle) | — | 0/10 (0%) | 0/10 (0%) |
| HBPG | 100 | 1/10 (10%) | 3/10 (30%) |
|  | 200 | 6/10* (60%) | 10/10* (100%) |
|  | 400 | 9/10* (90%) | 9/10* (90%) |
| foscarnet | 100 | 1/10 (10%) | 0/10 (0%) |
|  | 200 | 5/10* (50%) | 4/10* (40%) |
|  | 400 | 7/10* (70%) | 6/10* (60%) |

*p < 0.05

Table 2 illustrates the dose-response relationships for treatment of HSV2 encephalitis when the individual drugs were given as a combination by intraperitoneal (ip) injection.

TABLE 2

Effect of Combinations of HBPG and foscarnet against HSV2 encephalitis in mice

| Treatment | Dose, mg/kg ip, bid, 5 d | Survivors/treated (%) |
|---|---|---|
| Corn oil vehicle | — | 0/20 (0%) |
| HBPG | 50 | 1/10 (10%) |
| " | 100 | 3/10 (30) |
| Foscarnet | 50 | 0/10 (0%) |
| HBPG + foscarnet | 50 + 50 | 5/10* (50%) |
| " | 100 + 50 | 8/10* (80%) |

*p < 0.033

The results of Table 1 establish dose-response relationships for the effect of each compound when administered individually to mice to be used against encephalitis caused by HSV1 and HSV2. The results of Table 2 illustrate the effect of combining suboptimal doses of HBPG and foscarnet in treatment of HSV2 encephalitis, showing clear synergistic effect of the combinations. For example, the combination of 50 mg/kg of each compound protected 50% of mice from HSV2 encephalitis, whereas simple addition of the compound effects would be expected to protect only 10% of animals. The combination of 100 mg/kg of HBPG and 50 mg/kg of foscarnet protected 80% of mice from HSV2 encephalitis, whereas simple addition of the compound effects would be expected to protect 30% of animals.

The same experiment was repeated using HBPG and cidofovir, and the results are summarized in Tables 3 and 4.

TABLE 3

Effect of cidofovir on HSV1 and HSV2 encephalitis in mice

| Dose of cidofovir* | Survivors/treated (%) HSV1 | HSV2 |
|---|---|---|
| — (corn oil) | 0/10 (0%) | 0/10 (0%) |
| 1 mg/kg | 0/10 (0%) | 0/10 (0%) |
| 2.5 mg/kg | 3/10 (30%) | 4/10 (40%) |
| 5 mg/kg | 9/10 (90%) | 10/10 (100%) |

*Intraperitoneal injection in suspension in corn oil, twice daily for five days

TABLE 4

Effect of Combinations of HBPG and cidofovir against HSV1 and HSV2 encephalitis in mice

| Dose HBPG* | dose cidofovir* | Survivors/treated (%) HSV1 | HSV2 |
|---|---|---|---|
| — (corn oil) | — | 0/10 (0) | 0/10 (0) |
| 25 mg/kg | 2.5 mg/kg | 7/10 (70%) | 6/10 (60%) |
| 50 mg/kg | 2.5 mg/kg | 9/10 (90%) | 10/10 (100%) |
| 100 mg/kg | 2.5 mg/kg | 10/10 (100%) | 10/10 (100%) |

*Intraperitoneal injection of combined suspension in corn oil, twice daily for five days.

Tables 3 and 4 illustrate the dose-response relationships for treatment of HSV1 and HSV2 encephalitis by cidofovir alone and by combinations of HBPG and cidofovir given by intraperitoneal (ip) injection. The results of Table 3 establish dose-response relationship for the effect of cidofovir against encephalitis caused by HSV1 and HSV2, resulting in a median effective dose of 2.5-5 mg/kg. On the other hand, the results of Table 4 illustrate the effect of combining suboptimal doses of HBPG and a dose less than the median effective dose of cidofovir in treatment of HSV1 and HSV2 encephalitis. Table 4 shows a clear synergistic effect of the combinations against both infections. Combinations of 25 or 50 mg/kg of HBPG, doses which alone have no efficacy (see Table 1), with 2.5 mg/kg of cidofovir gave significantly increased protection of mice from both infections (60-100%), whereas simple addition of the compound effects would be expected to protect no more than 30-40% of animals. The combination of 100 mg/kg of HBPG with 2.5 mg/kg of cidofovir completely protected all animals from both infections, compared with expected protection of 60-70% of animals.

The experiment with HSV1 infected mice was repeated using HBPG and acyclovir, and the results are summarized in Tables 5 and 6.

TABLE 5

Effect of acyclovir on HSV1 encephalitis in mice

| Dose of acyclovir* | survivors/treated (%) |
|---|---|
| — (corn oil) | 0/10 (0) |
| 25 mg/kg | 1/10 (10%) |

TABLE 5-continued

Effect of acyclovir on HSV1 encephalitis in mice

| Dose of acyclovir* | survivors/treated (%) |
|---|---|
| 50 mg/kg | 3/10 (30%) |
| 100 mg/kg | 7/10 (70%) |

*Intraperitoneal injection in suspension in corn oil, twice daily for five days

TABLE 6

Effect of combinations of HBPG and acyclovir against HSV1 encephalitis in mice.

| Dose HBPG* | Dose acyclovir* | survivors/treated (%) |
|---|---|---|
| — (corn oil) | — | 0/10 (0) |
| 25 mg/kg | 50 mg/kg | 5/10 (50%) |
| 50 mg/kg | 50 mg/kg | 8/10 (80%) |
| 100 mg/kg | 50 mg/kg | 10/10 (100%) |

*Intraperitoneal injection of combined suspension in corn oil, twice daily for five days Tables 5 and 6 illustrate the dose-response relationship for treatment of HSV1 encephalitis by acyclovir alone and by combination of HBPG and acyclovir given by intraperitoneal (ip) injection. The results of Table 5 establish the dose-response relationship for the effect of acyclovir against encephalitis caused by HSV1, resulting in a median effective dose of between 50 and 100 mg/kg. On the other hand, the results of Table 6 illustrate the effect of combining suboptimal doses of HBPG and a dose less than the median effective dose of acyclovir in treatment of HSV1 encephalitis. Table 5 shows a clear synergistic effect of the combinations against the infection. Combinations of 25 or 50 mg/kg of HBPG, doses which alone have no efficacy (Table 1), with 50 mg/kg of acyclovir gave significantly increased protection of mice (50 and 80%, respectively), whereas simple addition of the compound effects would be expected to protect no more than 30% of animals. Combination of 100 mg/kg of HBPG with 50 mg/kg of acyclovir completely protected the animals (100% survival), compared with expected protection of 40%, i.e. from the additive effects of HBPG (10%) and acyclovir (30%).

Other Embodiments

A number of embodiments of the invention have been described. Nevertheless, it will be understood that various modifications can be made without departing from the spirit and scope of the invention. Accordingly, other embodiments are within the scope of the following claims.

What is claimed is:

1. A composition comprising a combination of:
   a) 2-phenylamino-9-(4-hydroxybutyl)-6-oxopurine, or an ester or salt thereof, and
   b) an antiherpes substance selected from the group consisting of acyclovir, ganciclovir, cidofovir, and foscarnet, or any combination thereof, or an ester or salt thereof.

2. The composition of claim 1, wherein the antiherpes substance is cidofovir or an ester or salt thereof.

3. The composition of claim 1, wherein the antiherpes substance is acyclovir, or an ester or salt thereof.

4. The composition of claim 1, wherein the antiherpes substance is ganciclovir, or an ester or salt thereof.

5. A dosage form for parenteral or oral use containing a pharmaceutical composition according to claim 1.

6. A cream, lotion, gel, ointment, plaster, stick, or pen containing a composition according to claim 1.

7. The composition of claim 1, including a pharmaceutically acceptable carrier that is selected from the group consisting of sterile water, saline, polyalkylene glycols, vegetable oils, hydrogenated naphthalenes, biocompatible polymers, biodegradable polymers, and mixtures thereof.

8. The composition of claim 7, wherein the biodegradable polymer is selected from the group consisting of polycaprolactone, polydecalactone, poly(sebacic anhydride), sebacic acid-co-1,3-bis(carboxyphenoxypropane), sebacic acid-co-1,6-bis(carboxyphenoxyhexane), dedecanoic-co-1,3-bis(carboxyphenoxypropane), dedecanoic-co-1,6-bis(carboxyphenoxyhexane), albumin and derivatives, gelatin and derivatives, starch and derivatives, gum arabic, cellulose and derivatives, polysorbate and derivatives, agarose, lectins, galactose, polyurethanes, polyvinylalcohol, functionalized polymers and copolymers of lactic and glycolic acid, lactic acid homopolymer, glycolic acid copolymer, copolymers of lactic acid and glycolic acid, polyhydroxybutyrate, polyhydroxyalkanoic acid, and mixtures thereof.

9. The composition of claim 8, wherein the biodegradable polymer is in the form of a particle.

10. The composition of claim 9, wherein the particle includes multiple walls.

11. A kit for treatment of a Herpes simplex virus infection in a mammal, the kit comprising:
   a) 2-phenylamino-9-(4-hydroxybutyl)-6-oxopurine, or an ester or salt thereof,
   b) an antiherpes substance selected from the group consisting of acyclovir, ganciclovir, cidofovir, and foscarnet, or any combination thereof, or an ester or salt thereof, and
   c) instructions for administering (a) and (b) concurrently or within a sufficiently close time to achieve coexistent concentrations Of (a) and (b) in subject.

12. The kit of claim 11, wherein the antiherpes substance is cidofovir or an ester or salt thereof.

13. The kit of claim 11, wherein the antiherpes substance is acyclovir, or an ester or salt thereof.

14. The kit of claim 11, wherein the antiherpes substance is granciclovir, or an ester or salt thereof.

15. The kit of claim 11, wherein the kit comprises 2-phenylamino-9-(4-hydroxybutyl)-6-oxopurine, or an ester or salt thereof, and the antiherpes substance acyclovir, or an ester or salt thereof.

16. The composition of claim 1 comprising a combination of 2-phenylamino-9-(4-hydroxybutyl)-6-oxopurine, or an ester or salt thereof, and the antiherpes substance acyclovir, or an ester or salt thereof.

17. A method for treating a recurrent Herpes simplex virus infection in a mammal, the method comprising administering to the mammal a therapeutic dose of the composition of claim 1.

18. A method for treating a Herpes simplex virus infection in a mammal, the method comprising obtaining the kit of claim 11 and administering the inhibitor and antiherpes substance according to the instructions.

19. A composition comprising a combination of:
   a) 2-phenylamino-9-(4-hydroxybutyl)-6-oxopurine, or an ester or salt thereof; and
   b) an antiherpes substance selected from the group consisting of foscarnet or an ester or salt thereof; acyclovir, or an ester or salt, and cidofovir or an ester or salt thereof.

20. The composition of claim 19, wherein the antiherpes substance comprises acyclovir or an ester or salt thereof.

21. A kit for treatment of a Herpes simplex virus infection in a mammal, the kit comprising:

a) 2-phenylamino-9-(4-hydroxybutyl)-6-oxopurine, or an ester or salt thereof;

b) an antiherpes substance selected from the group consisting of foscarnet or an ester or salt thereof, acyclovir, or an ester or salt thereof; and cidofovir or an ester or salt thereof, and c) instructions for administering (a) and (b) concurrently or within a sufficiently close time to achieve coexistent concentrations of (a) and (b) in subject.

22. The kit of claim 21, wherein the antiherpes substance comprises acyclovir or an ester or salt thereof.

* * * * *

UNITED STATES PATENT AND TRADEMARK OFFICE
CERTIFICATE OF CORRECTION

PATENT NO. : 7,727,995 B2  Page 1 of 1
APPLICATION NO. : 10/767019
DATED : June 1, 2010
INVENTOR(S) : George E. Wright It is certified that error appears in the above-identified patent and that said Letters Patent is hereby corrected as shown below:

On the Title Page:

First Page, Column 2 (Other Publications)

Line 4, delete "Metabloism" and insert -- Metabolism --

Line 9, delete "Anitviral" and insert -- Antiviral --

Line 16, delete "Synethesis" and insert -- Synthesis --

Line 17, delete "Inhhibitors" and insert -- Inhibitors --

In the Claims:

Column 12

Line 12, in Claim 8, delete "dedecanoic" and insert -- dodecanoic --

Line 13, in Claim 8, delete "dedecanoic" and insert -- dodecanoic --

Line 35, in Claim 11, delete "Of" and insert -- of --

Line 41, in Claim 14, delete "granciclovir," and insert -- ganciclovir, --

Line 62, in Claim 19, delete "thereof;" and insert -- thereof, --

Column 13

Line 5, in Claim 21, delete "thereof;" and insert -- thereof, --

Signed and Sealed this

Twenty-fourth Day of August, 2010

David J. Kappos
*Director of the United States Patent and Trademark Office*